United States Patent [19]
Nordan

[11] Patent Number: 5,133,749
[45] Date of Patent: Jul. 28, 1992

[54] CENTRATING HAPTICS

[76] Inventor: Lee T. Nordan, 9834 Genesee Ave., Ste. 209, La Jolla, Calif. 92037

[21] Appl. No.: 698,969

[22] Filed: May 13, 1991

[51] Int. Cl.⁵ .................................. A61F 2/16
[52] U.S. Cl. .................................. 623/6
[58] Field of Search ........................ 623/6

[56] References Cited

U.S. PATENT DOCUMENTS

| | | | |
|---|---|---|---|
| 4,242,760 | 1/1981 | Rainin | 623/6 |
| 4,576,607 | 3/1986 | Kelman | 623/6 |
| 4,710,195 | 12/1987 | Giovinazzo | 623/6 |
| 4,813,955 | 3/1989 | Achatz et al. | 623/6 |
| 4,871,363 | 10/1989 | Kelman | 623/6 |
| 4,990,159 | 2/1991 | Kraff | 623/6 |

Primary Examiner—Randy C. Shay
Attorney, Agent, or Firm—Henri J. A. Charmasson

[57] ABSTRACT

An intra-ocular lens for implanting into the posterior capsule after cataract extraction, has a pair of sinuous haptics having greater flexibility near their roots than at their distal ends. A long arcuate distal segment of each haptic espouses the internal radius of the posterior capsule over an arc of at least 15 degrees. Both haptics have a slight backward slant. The haptics facilitate the implantation and retention of the lens.

4 Claims, 2 Drawing Sheets

CENTRATING HAPTICS

FIELD OF THE INVENTION

This invention relates to extra-ocular lens prosthesis which are commonly installed after an intra-capsular cataract extraction into the posterior chamber or into the capsular bag. More specifically, this invention relates to the fixation appendages or haptics associated with the intra-ocular lens.

BACKGROUND OF THE INVENTION

As part of the surgical procedure commonly known as extracapsular cataract extraction, during which the anterior capsule is extracted with the lens and the posterior capsule is drained but left intact, an artificial lens is installed into the posterior capsule. As illustrated in FIGS. 1-3, the artificial intra-ocular lens (IOL) 1 is provided with two integrally formed appendages or haptics 2,3 which are designed to centrally mount the IOL while nesting into the inner peripheral rim 4 of the posterior capsule. It is estimated that in half of such surgical interventions, one of the haptics 2, 3 is not retained into the rim of the posterior capsule by its anterior flaps 5 and instead bears against the ciliary sulcus 6, or is erroneously implanted in that position, as illustrated in FIG. 1. This asymmetrical position of the IOL results in a decentration whereby the axis XX' of the IOL is shifted away from the actual axis Y—Y' of the eye. There results a loss of visual acuity which often evades the attention of the ophthalmologist.

SUMMARY OF THE INVENTION

The principal and secondary objects of this invention are to reduce or eliminate the risk of eccentric installation or movement of an IOL installed in the posterior capsule; and to facilitate the manipulation of the IOL and its placement in the posterior capsule.

These and other objects are achieved by increasing the lengths and sinuosity of the haptics and providing for a stiffer resistance to bending in their distal portions, as well as angling the haptics backward from the vertical axis of the IOL.

DESCRIPTION OF THE PREFERRED EMBODIMENT OF THE INVENTION

Figure 4:
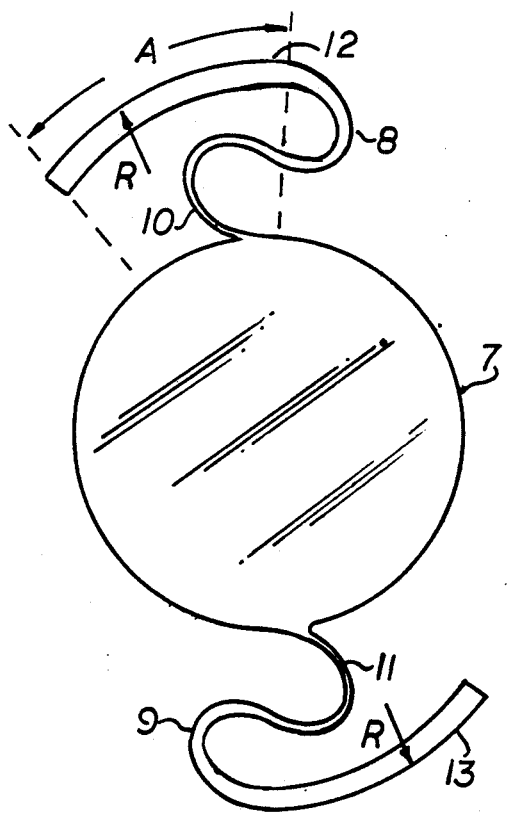
FIG. 4 is a front elevational view of an intra-ocular lens according to the invention.
Figure 5:
FIG. 5 is a right side elevational view thereof.

The preferred embodiment of the invention is illustrated in FIGS. 4 and 5. An intraocular lens (IOL) 7 of generally same shape and dimensions as the IOL of the prior art has a pair of integrally formed haptics 8, 9 projecting from diametrically opposed points on the periphery of the IOL. Each haptic is formed into a sinuous curve and characterized by a difference in thickness and consequently in flexibility between sections. In this embodiment a proximal section 10, 11 near its root on the IOL has a substantially smaller cross-section than the cross-section of a distal portion 12, 13. The distal section 12, 13 describes an arc of at least 15 degrees at a constant radius R corresponding to the radius of the posterior capsule into which the IOL is to be mounted. The preferred embodiment is further characterized by a backward slanting at the haptics by an angle B in a range of 3 to 15 degrees. In this embodiment, each haptic has a continuously increasing cross-section as it extends away from the optic. The variations in the cross-section results in a higher degree of flexibility of any portion of the haptic closer to the optic as compared to a more distal portion.

Figure 1:
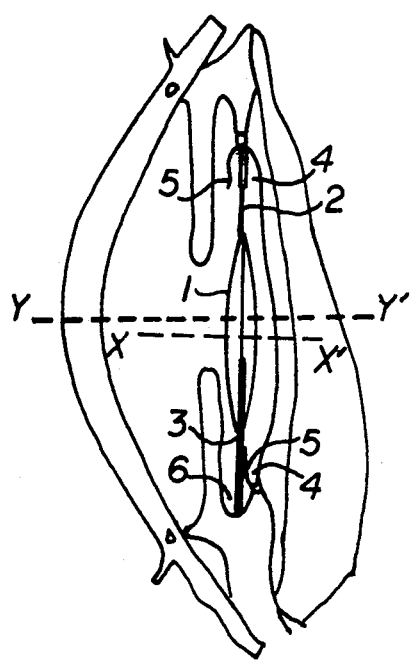
FIG. 1 illustrates a decentrated implantation of an intraocular lens.
Figure 2:
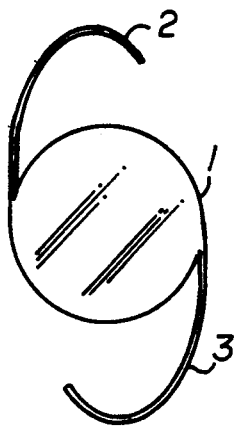
FIG. 2 is a front elevational view of a prior art lens.
Figure 3:
FIG. 3 is a right side elevational view thereof.

The just described configuration of the haptics facilitates the installation of the IOL into the capsular bag and greatly increases its stability. When, during installation, the haptics are compressed to clear the flaps 5 of the posterior capsule illustrated in FIG. 1, the proximal section 10 flexes first without substantial deformation of the more distal sections 12, 13. This phenomenon accounts for a more convenient handling and manipulation of the IOL into the posterior capsule. Once installed, the more rigid distal sections 12, 13 retain their common radius R with the interior of the capsule, and through their extended length and increased thickness, present a substantially larger contact area with the interior rim 4 of the posterior capsule. The increased friction between the haptics and the lining of the posterior capsule assure a more stable placement of the prosthesis. The slight backward angle B of the haptics places the optic in the very center of the posterior capsule where it is less likely to be contacted by its posterior wall and knocked out of alignment as frequently occurred with devices of the prior art.

Figure 6:
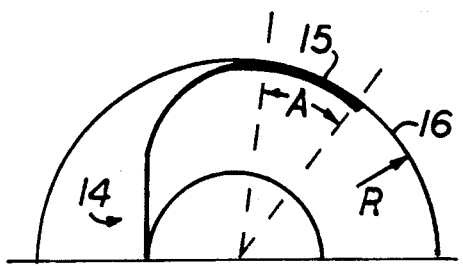
FIGS. 6-9 are diagrammatical illustrations of various alternate haptic configurations.

In the first alternate configuration of the haptic 14 diagrammatically illustrated in FIG. 6, the general arcuate shape common to the haptics of the prior art has been retained, but the stiffer distal portion 15 espouses the radius of curvature R of the posterior capsule 16 over an arc A of no less than 15 degrees.

Figure 7:
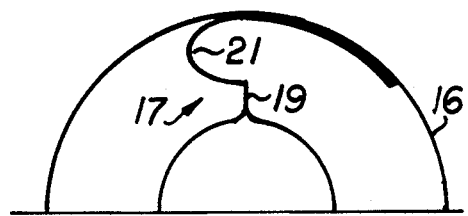
Figure 8:
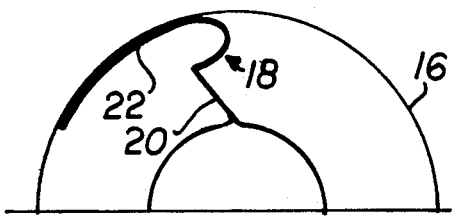
Figure 9:
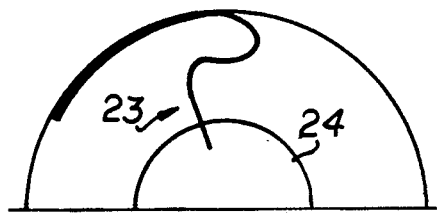

In the second and third alternate embodiments 17, 18 illustrated in FIGS. 7 and 8, the haptics are characterized by a first linear, proximal section 19, 20 of relatively low flexibility, followed by an arcuate section 21, 22 with the same characteristics as the first embodiment, i.e. decreasing flexibility, common radius of curvature, and increased contact arc with the rim of the posterior capsule 16. In the fourth alternate embodiment 23, the haptics are not built integrally with the optic 24 but are made from a different material and implanted therein.

Figure 10:
FIG. 10 is a perspective view of a section of an alternate embodiment of the haptic.

The haptic segment 25 illustrated in FIG. 10 has a portion 26 with an arcuate cross-section reinforced by a radial rib 27. The variation in flexibility can be achieved by variations in the width or thickness of the radial rib 27 in lieu of, or in addition to, variations in the thickness and width of the arcuate portion 26. It should also be noted that the difference between the flexibility of the proximal and distal portions need not necessarily be progressive and could be achieved by a sudden transition at mid-length of the haptic. Such a difference in the flexibility of the two segments of the haptics can be achieved by use of different materials while keeping a constant cross-section along the entire length of the haptic.

While the preferred embodiments of the invention have been described, modifications can be made and other embodiments may be devised without departing from the spirit of the invention and the scope of the appended claims.

What is claimed is:

1. In combination with an intra-ocular lens implantable into the capsular bag following cataract extraction, a pair of flexible haptics projecting from diametrically opposed peripheral points of the lens into symmetrical arcuate shapes, each haptic comprising a first segment having a root end at one of said peripheral points, and a second segment extending continuously from a junction point with said first segment of a distal end;
   wherein the flexibility of at least one of said segments varies continuously between said junction point and one of said ends
   wherein one of said segments has a cross-section comprising an arcuate segment and a radial linear segment projecting from a median section of said arcuate segment.

2. In combination with an intra-ocular lens implantable into the capsular bag following cataract extraction, a pair of flexible haptics projecting from diametrically opposed peripheral points of the lens into symmetrical arcuate shapes, each haptic comprising a first segment having a root end at one of said peripheral points, and a second segment extending continuously from a junction point with said first segment to a distal end;
   wherein the flexibility of at least one of said segments varies continuously between said junction point and one of said ends;
   wherein the flexibility of each first segment increases progressively between the root end and the junction point.

3. The combination of claim 1, wherein each second segment has a larger median cross-section than the median cross-section of the first segment.

4. The combination of claim 3, wherein the flexibility of each second segment increases progressively between the junction point and the distal end.

* * * * *